(12) United States Patent
Donitzky et al.

(10) Patent No.: US 6,328,732 B1
(45) Date of Patent: Dec. 11, 2001

(54) DEVICE FOR TREATING BODILY SUBSTANCES

(75) Inventors: Christof Donitzky, Eckental; Arnold Pribbernow, Simmelsdorf, both of (DE)

(73) Assignee: Wavelight Laser Technologies GmbH, Erlangen (DE)

( * ) Notice: Subject to any disclaimer, the term of this patent is extended or adjusted under 35 U.S.C. 154(b) by 0 days.

(21) Appl. No.: 09/319,654

(22) PCT Filed: Oct. 20, 1997

(86) PCT No.: PCT/EP97/05786

§ 371 Date: Jun. 10, 1999

§ 102(e) Date: Jun. 10, 1999

(87) PCT Pub. No.: WO98/25529

PCT Pub. Date: Jun. 18, 1998

(30) Foreign Application Priority Data

Dec. 10, 1996 (DE) .......................................... 296 21 429 U
Apr. 8, 1997 (DE) .............................................. 197 14 476

(51) Int. Cl.$^7$ .................................................. A61B 18/18
(52) U.S. Cl. ................................. 606/11; 606/10; 606/13; 606/4; 606/6; 606/9; 606/3; 607/89; 433/215
(58) Field of Search ..................... 606/10–15, 2–6, 606/9, 17, 18; 433/215

(56) References Cited

U.S. PATENT DOCUMENTS

| | | |
|---|---|---|
| 4,372,315 | 2/1983 | Shapiro et al. . |
| 4,572,189 | 2/1986 | Smith et al. . |
| 4,933,843 | 6/1990 | Scheller et al. . |
| 5,002,051 * | 3/1991 | Dew et al. .......................... 128/395 |
| 5,263,951 * | 11/1993 | Spears et al. .......................... 606/12 |
| 5,269,778 * | 12/1993 | Rink et al. .............................. 606/12 |
| 5,275,594 * | 1/1994 | Baker et al. ............................ 606/12 |
| 5,401,171 | 3/1995 | Paghdiwala . |

(List continued on next page.)

FOREIGN PATENT DOCUMENTS

| | | | |
|---|---|---|---|
| 0 065 223A1 | 11/1982 | (EP) | ................................. H01S/3/10 |
| 0 164 751A2 | 12/1985 | (EP) | ............................... H01S/3/097 |
| 0 194 856A2 | 9/1986 | (EP) | ................................. A61F/9/00 |
| PCT WO 89/03202 | 4/1989 | (WO) | ............................... A61F/9/00 |
| PCT WO 95/17130 | 6/1995 | (WO) | ............................. A61B/17/36 |

OTHER PUBLICATIONS

Ray P. Gailitis et al. Comparison of Laser Phacovaporization Using the Er–YAG and the Er–YSGG Laser, Arch. Ophthalmol, vol. 111, May 1993, p. 697–700.

German Document G–24500, Handbuch und Bedienungsanleitung, für eine Ultraschallgeräteeinheit Phaco–Aspitron I/A–System, Ausgabe, Sep. 1991.

W. Boke *Phakoemulsifikation. Warum?* Klin. Mbl. Augenheilk., 197 (1990) pp. 100–105.

Jeffrey W. Berger et al. *Temperature measuring during phacoemulification and erbium: YAG laser phacoablation in model systems*, Journal of Cataract Refract Surg., vol. 22, Apr. 1996, pp. 372–378.

*Primary Examiner*—Linda C. M. Dvorak
*Assistant Examiner*—Ahmed Farah
(74) *Attorney, Agent, or Firm*—Clifford W. Browning; Woodard, Emhardt, Naughton, Moriarty & McNett

(57) ABSTRACT

A device for treating bodily substances, in particular for intraocular cataract surgery, said device comprising a laser beam source, for example, an erbium YAG laser, which produces pulsed laser radiation at wavelengths in the infrared range. A control device comprises a first arrangement (38, 48) by means of which an acceptable range for the pulse energy and/or pulse length and/or pulse frequency can be predetermined before an operation, and a second arrangement (34, 36, 40, 42) by means of which the pulse energy and/or pulse length and/or pulse frequency can be adjusted to a given value or values within the predetermined range during the operation.

10 Claims, 1 Drawing Sheet

U.S. PATENT DOCUMENTS

| | | | |
|---|---|---|---|
| 5,423,798 | * | 6/1995 | Crow .......................................... 606/4 |
| 5,456,603 | * | 10/1995 | Kowalyk et al. ..................... 433/215 |
| 5,554,894 | | 9/1996 | Sepielli . |
| 5,580,347 | | 12/1996 | Reimels . |
| 5,782,822 | * | 7/1998 | Telfair et al. ............................. 606/5 |
| 6,056,742 | * | 5/2000 | Murphy-Chutorian et al. ........ 606/11 |
| 6,074,382 | * | 6/2000 | Asaha et al. ............................. 606/9 |

* cited by examiner

DEVICE FOR TREATING BODILY SUBSTANCES

The invention relates to a device for treating bodily substances, comprising a laser beam source which produces pulsed laser radiation at wavelengths particularly in the infrared range, an arrangement for guiding the laser radiation to the location of treatment, and further comprising a control device by means of which the pulse energy and/or pulse length and/or pulse frequency can be adjusted.

Quite generally, the invention is suitable for treating bodily substances, i.e. producing an effect on bodily substances in many different ways. The term "treatment" may either refer to changing the conditions of these substances, or to removing these substances from the body, or to changing the position of the substances in the body. The bodily substances can be manifold, for example diseased tissue, or a substance generated in diseased form, or tissue which is sound per se but is to be removed for medical reasons. The following is a description of the invention with regard to what is known as intraocular cataract surgery.

A cataract is a change of the lens of the human eye, resulting in loss of transparency of the visible optical range of the lens. The region of the lens becomes cloudy. Loss of transparency causes impairment of vision.

Cataract surgery refers to the surgical treatment of the cataract, wherein the cloudy lens is removed from the path of light beams required for the optical perception. During the past centuries, such removal was done by what is known as cataract cracking, and the patient was then given so-called cataract lenses.

In 1949, the British ophtalmologist H. Ridley was the first to implant an artificial lens (PMMA) into the patient's eye after a cataract operation.

Accordingly, before implanting an interocular (new) lens, cataract surgery requires the original cloudy lens to be removed.

One criterion in cataract surgery recognised as being of growing importance is the fact that as much neighboring tissue structures as possible are to be maintained while the cloudy lens is being removed.

The surgical technique differentiates between the so-called intracapsular lens dispensation and the extracapsular cataract extraction. In the last-mentioned method it is the aim of the operation to remove the cloudy lens from the capsule of the lens, with the intention to leave said capsule of the lens in its anatomic position as much as possible.

Lately, the so-called phacoemulsification has been developed as an example for extracapsular cataract surgery (W. B öke "Phakoemulsifikation. Warum?", Klin. Mbl. Augenheilk., 197 (1990) 100–105, F. Enke publishing house of Stuttgart). Basically, phacoemulsification is a standard surgical operation performed by means of a cut.

To reduce irritations of the tissue caused by cuts and other manipulations of the tissue, the so-called ultrasonic phacoemulsification has lately been used to a larger extent (see Jeffrey W. Berger, Jonathan H. Talamo, Keven J. LaMarche, Seon-Ho Kim, Robert W. Snyder, Donald J. D'Amico, George Marcellino "Temperature Measuring During Phacoemulsification and Erbium: YAG Laser Phacoablation in Model Systems", Journal of Cataract Refract Surg., Vol. 22, April 1996, pp. 372 to 378). Due to such ultrasonic phacoe-mulsification, both the interoperative stresses as well as the postoperative complications may largely be reduced to a minimum. By means of this technique, the material of the lens is removed via an aspiration/irrigation system. The energy used to crack the lens is caused by ultrasonic vibrations which are applied to the body of the lens.

The energy required to crack the cloudy lens can also be provided by means of laser radiation (also see the above-mentioned article of J. W. Berger et al). In case of the so-called laser phacovaporization, for example by means of Er- YAG- or Er-YSGG lasers, the material of the lens is broken, due to the high absorption of the laser radiation in the IR region in the tissue to be treated, such cracking resulting in tissue ablation or tissue separation (Ray P. Gailitis, Scott W. Patterson, Mark A. Samuels, Kerry Hagen, Qiushi Ren, George O. Waring "Comparision of Laser Phacovaporization Using the Er-YAG and the Er-YSGG Laser", Arch Ophtamol, Vol. 111, May 1993, pp. 697–700).

The present invention relates to the removal of a cloudy lens by use of laser.

Said above-mentioned problems do not only occur in cataract surgery but generally in treating substances of the human body ("bodily substances") with laser radiation. When treating bodily substances with laser radiation it is generally important to treat only the diseased or changed regions by means of such radiation, whilst more or less adjacent regions should at best not be exposed to such radiation.

U.S. Pat. No. 4,572,189 describes an electronic control device for a surgical laser system in which only the maximum pulse number and two pulse durations can be predetermined. U.S. Pat. No. 4,933,843 and EP-A-0164751 describe surgical laser systems in which unsatisfactory adjustments of the system can be recognised by means of a menu control.

When used in cataract surgery, the invention relates to the technical problems arising from the different material of the lenses of different patients and from the non-homogeneity of the optical properties within a lens, and it is the object of the invention to provide a device for the intraocular cataract surgery as mentioned in the beginning so that the surgeon can be given a device which enables him to control the intraocular application of the laser energy to such an extent that it may be possible for him to remove the cloudy lens carefully without impairing the adjacent structures of the tissue.

According to the invention, this object relating to a device for the intraocular cataract surgery as mentioned above is solved in that the control device comprises a first arrangement by means of which an acceptable range for the pulse energy and/or pulse length and/or pulse frequency can be predetermined extent that the sound tissue remains unafflicted to the utmost amount.

When used in cataract surgery, the invention relates to the technical problems arising from the different material of the lenses of different patients and from the non-homogeneity of the optical properties within a lens, and it is the object of the invention to provide a device for the intraocular cataract surgery as mentioned in the beginning so that the surgeon can be given a device which enables him to control the intraocular application of the laser energy to such an extent that it may be possible for him to remove the cloudy lens carefully without impairing the adjacent structures of the tissue.

According to the invention, this object relating to a device for the intraocular cataract surgery as mentioned above is solved in that the control device comprises a first arrangement by means of which an acceptable range for the pulse energy and/or pulse length and/or pulse frequency can be predetermined before an operation, and a second arrangement by means of which the pulse energy and/or pulse length and/or pulse frequency can be adjusted to a given value or values within the predetermined range during the operation.

The invention is in particular also suitable for devices used in dermatology, particularly for the treatment of scars or wrinkles. When used in dermatology, fibrous material or an articulated arm with mirror as known per se can also be used as guide means, i.e. the radiation is guided to the required location via mirrors.

Furthermore, the invention is also suitable for devices used in dentology, in particular for the treatment of hard tooth substances such as dental enamel or dentin.

When used in dentology, an Er:YAG solid-state laser is particularly suitable as laser radiation source, and this preferably even in combination with another laser such as a Nd:YAG solid-state laser (wavelength: 1064 nm). It is preferred to use said two lasers in alternating manner via two different guide means, however, with the same control device according to the invention being provided for pulse energy, pulse length or pulse frequency.

The invention enables the surgeon to easily reduce the applied energy of laser radiation drastically if, for example, the location of energy supply approaches a critical region, for example an adjacent tissue structure like the capsular sac which should at best be preserved. Accordingly, the invention allows, on the one side, to adjust the energy of laser radiation respectively applied during the operation, depending on the location where the laser radiation acts and on how far the operation has proceeded and, on the other side, to restrict the pulse energy and/or pulse length and/or pulse frequency which can be adjusted at all so that it can be ensured that only little energy or radiation of undesired pulse length and/or pulse frequency is applied (e.g. inadvertently) during the operation.

Accordingly, the invention allows the operation to be done in efficient (especially fast) and controlled manner under controlled and monitored energy supply, while the surgeon can predetermine in advance an admissible range for the pulse energy and/or pulse frequency and/or pulse length which can be adjusted at all in judging the material to be treated, e.g. the material of the lens, which appears to be optimal for the material to be treated. During the operation (interoperative), the desired parameters (pulse energy, pulse length or pulse frequency) may immediately be change by the surgeon by means of a simple handling system such as an adjusting element which may either be actuated by hand or by foot, depending on the stage of the operation and the material just being treated as well as on the location where the radiation acts. This enables the surgeon to react in definitely improved manner on individual differences in the tissue of the lens during the operation and when he reaches adjacent of the tissue which are to be preserved.

Preferred embodiments of the invention are described in the dependent claims.

An example of the invention for intraocular cataract surgery will be explained in more detail by means of the drawings, in which.

Figure 1:
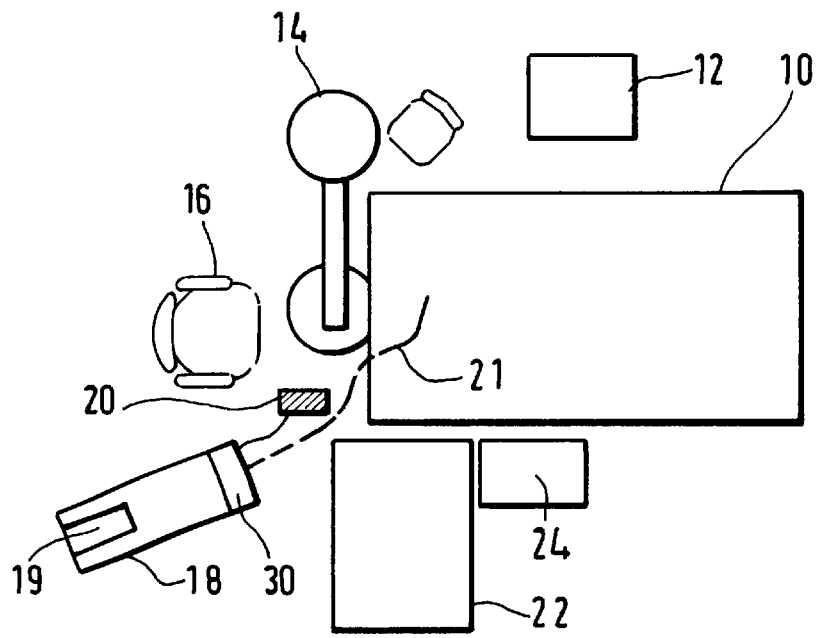
FIG. 1 is a schematic view of a device for intraocular cataract surgery

According to FIG. 1, a patient is placed on a bed 10. An anaesthetic and diagnostic system was given reference number 12, and an OPMI (operation microscope) was given reference number 14. The surgeon sits on a chair 16. A laser radiation source 19 is provided in a phaco ablation system 18. The laser radiation source 19 is an erbium YAG-laser. The laser output radiation is transmitted to the patient's eye by means of a fibre optics 21. This technique corresponds to the prior art and need not to be explained in more detail.

The surgeon may either adjust the pulse energy and/or pulse length and/or particularly pulse frequency (pulse repetition frequency) by means of a foot-actuated switch 20.

FIG. 1 shows an aspiration and irrigation system 22 for removing the fragments of the lens. In addition to the aspiration and irrigation system 22, a monitor 24 (for example also a video) is provided for the surgeon.

Figure 2:
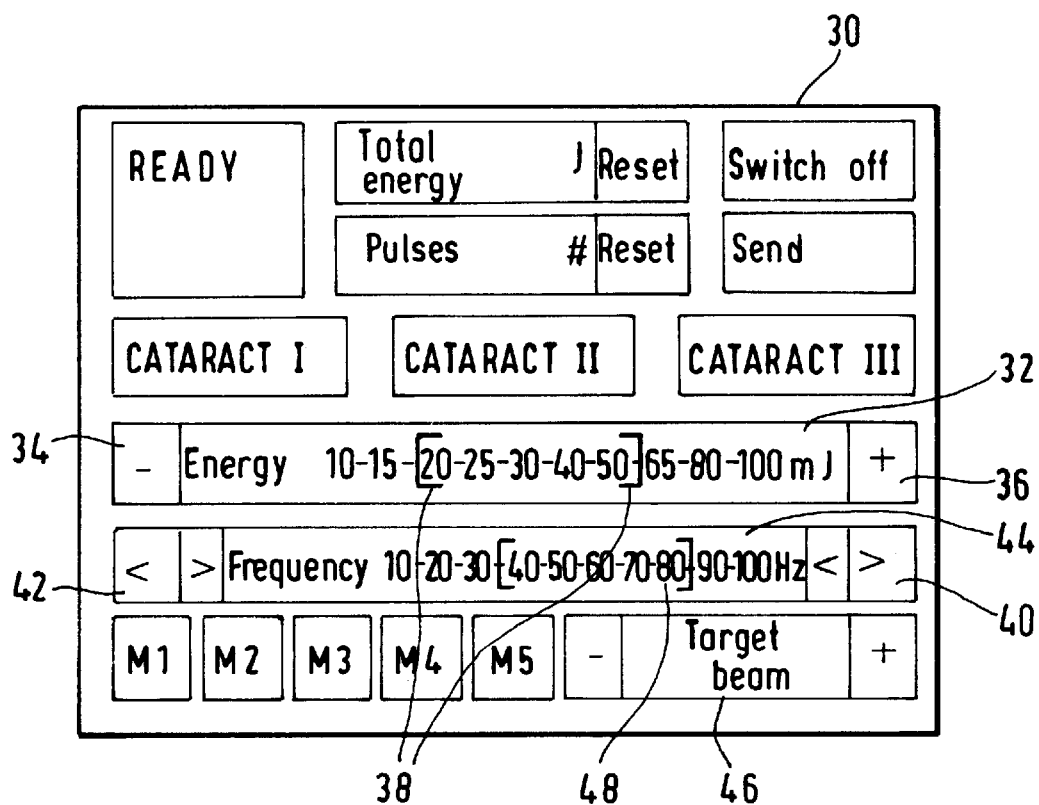
FIG. 2 is a schematic view of a control device for intraocular cataract surgery.

As concerns the control device 30 which has been integrated into the phaco ablation system 18, the key fields and functions with reference numbers 32 to 48 as shown in FIG. 2 are here of special interest. A field 32 shows different energy values for the adjustable pulse energy, viz. 10 mJ, 15 mJ, etc. to 100 mJ (pulse energy). Upper and lower limits for adjustable pulse energies can either be predetermined before an operation in the "energy field" 32 via a keyboard (not shown in detail) or changed during an operation. These limits are shown in FIG. 2 in brackets 38. Accordingly, said brackets 38 set the limits for admissible adjustable pulse energy values which means that, in case of the embodiment shown in FIG. 2, the surgeon may adjust twenty to fifty mJ pulse energy. The pulse energy may, for example, be changed during the operation by means of the two keys 34, 36. As soon as the minimum pulse energy value (20 mJ) has been set by the computer after having determined the limit value 38, the surgeon may gradually increase the pulse energy to 25 mJ, 30 mJ, etc. by pressing the "+" key 36, wherein each respectively valid pulse energy value is emphasized, for example, by bright lightening of the pulse energy value respectively set.

Field 44 of the control device 30 shows adjustable pulse repetition frequencies, with frequencies of 10 to 100 Hz being gradually adjustable by the surgeon. Such adjustment is being done by means of the keys 40 or 42 (increase or decrease of frequency). The device may optionally be such that alternatively or additionally to the pulse energy range which can be adjusted before the operation (range limits 38) the pulse repetition frequency may also be adjusted in advance as concerns the frequencies available at all, which is shown in FIG. 2 by bracket 48 acting analogously with regard to the above-described bracket 38 concerning the pulse energy.

The device comprises a so-called target beam to indicate the surgeon the position of the non-visible IR laser beam. Such target beam may be, for example, the beam supplied by a laser diode in the visible range (e.g. 635 nm). The laser diode for the target beam is provided in the phaco ablation system 18, and the radiation is also transmitted via the fibre optics 21.

What is claimed is:

1. A device for treating bodily substances, comprising a laser beam source (19) which produces pulsed laser radiation, guide means (21) for guiding the laser beam to the location of treatment, and further comprising a control device (30) by means of which at least one of the parameters selected from the group consisting of the pulse energy, pulse length and the pulse frequency can be adjusted, wherein said control device (30) comprises a first means (38, 48) for predetermining, before an operation, an acceptable range for at least one of the parameters selected from the group consisting of the pulse energy, the pulse length, and the pulse frequency, said range having a minimum value different from zero, and said control device (30) comprising a foot switch (20) that can be actuated by a surgeon for quickly adjusting at least one parameter selected from the group comprising the pulse energy, the pulse length, and the pulse frequency within the predetermined range during the operation.

2. A device according to claim 1, characterised in that an admissible range (38) can be predetermined for the pulse energy by means of the control device (30) and in that a value within said predetermined range may optionally be adjusted during the operation.

3. A device according to claim 1, characterised in that an admissible range can be predetermined for the pulse repetition frequency by means of the control device and in that a value within said predetermined range may optionally be adjusted during the operation.

4. A device according to claim 1, characterised in that laser radiation is produced by the laser beam source in the infrared range.

5. A device according to claim 4, characterized in that laser radiation is produced by the laser beam source in the middle infrared range.

6. A device according to claim 1 for use in intraocular cataract surgery, characterized in that said guide means (21) is designed in such a manner that the laser radiation can be applied to ocular tissue.

7. A device according to claim 1, characterised in that said guide means is designed in such a manner that the laser radiation can be applied to tooth material.

8. A device according to claim 1, characterised in that the laser radiation can be applied to skin by means of the guide means, wherein fiber material or an articulated arm with mirror is provided for said guide means.

9. A device according to claim 1, characterized in that the laser beam source is a solid-state laser doped with erbium.

10. A device according to claim 1, characterized in that the solid-state laser source is an erbium YAG laser source.

* * * * *